US008003125B2

(12) United States Patent
Li et al.

(10) Patent No.: US 8,003,125 B2
(45) Date of Patent: Aug. 23, 2011

(54) INJECTABLE DRUG DELIVERY SYSTEMS WITH CYCLODEXTRIN-POLYMER BASED HYDROGELS

(75) Inventors: Jun Li, Singapore (SG); Hanry Yu, Singapore (SG); Kam Leong, Ellicott City, MD (US)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 09/861,182

(22) Filed: May 18, 2001

(65) Prior Publication Data

US 2002/0019369 A1 Feb. 14, 2002

(30) Foreign Application Priority Data

May 19, 2000 (SG) ............................... 200002754-0

(51) Int. Cl.
*A61K 9/52* (2006.01)
(52) U.S. Cl. ......................................... 424/457; 514/58
(58) Field of Classification Search ................... 514/54, 514/58; 536/102, 103, 114, 123.1, 124; 424/484, 424/486, 487, 488, 422, 423; 523/54.2
See application file for complete search history.

(56) References Cited

U.S. PATENT DOCUMENTS

| | | | | |
|---|---|---|---|---|
| 4,179,337 A | | 12/1979 | Davis et al. ................. | 435/181 |
| 4,449,938 A | * | 5/1984 | Pollak .......................... | 523/116 |
| 4,609,546 A | | 9/1986 | Hiratani ....................... | 424/83 |
| 5,143,724 A | | 9/1992 | Leshchiner et al. ........ | 424/78.08 |
| 5,256,652 A | | 10/1993 | El-Rashidy .................. | 514/58 |
| 5,298,410 A | * | 3/1994 | Phillips et al. .............. | 435/188 |
| 5,324,718 A | | 6/1994 | Loftsson ..................... | 514/58 |
| 5,324,775 A | | 6/1994 | Rhee et al. .................. | 525/54.2 |
| 5,413,797 A | | 5/1995 | Khan et al. .................. | 424/489 |
| 5,472,954 A | | 12/1995 | Loftsson ...................... | 514/58 |
| 5,482,719 A | | 1/1996 | Guillet et al. ............... | 424/486 |
| 5,855,900 A | * | 1/1999 | Nobuhiko ................... | 424/425 |
| 5,922,340 A | | 7/1999 | Berde et al. ................. | 424/426 |
| 5,939,453 A | | 8/1999 | Heller et al. ................ | 514/58 |
| 5,942,241 A | | 8/1999 | Chasin et al. ............... | 424/426 |
| 5,968,543 A | | 10/1999 | Heller et al. ................ | 424/425 |
| 6,083,534 A | | 7/2000 | Wallach et al. ............. | 424/484 |
| 6,096,303 A | * | 8/2000 | Fick ............................ | 424/93.2 |
| 6,331,311 B1 | | 12/2001 | Brodbeck et al. .......... | 424/425 |

FOREIGN PATENT DOCUMENTS

| | | |
|---|---|---|
| EP | 0 154 316 | 9/1985 |
| EP | 0 510 356 | 10/1992 |
| WO | 94/01483 | 1/1994 |
| WO | 94/14421 | 7/1994 |
| WO | 95/05164 | 2/1995 |
| WO | 95/11924 | 5/1995 |
| WO | 98/55148 | 12/1998 |
| WO | 99/09149 | 2/1999 |
| WO | 00/33885 | 6/2000 |
| WO | 00/40962 | 7/2000 |
| WO | 00/50007 | 8/2000 |
| WO | 00/64977 | 11/2000 |

OTHER PUBLICATIONS

Li et al. Polymer Journal, 1994, vol. 2, pp. 1019-1026.*
Jeong et al. Nature, 1997, vol. 388, pp. 860-862.*
Amiel, C. et al., "New Associating Polymer Systems Involving Water Soluble Beta-Cyclodextrin Polymers," J. Inclusion Phen. Mol. Recog., 1996, 25, 61-67.*
Li, J et al., Sol-Gel Transition during Inclusion Complex Formation between alpha Cyclodextrin and High Molecular Weight Poly(ethylene glycol)s in Aqueous Solution. Polymer Journal. vol. 26 No. 9 pp. 1019-1026 (1994).*
Jeong et al., "biodegradable block copolymers as injectable drug-delivery system," Nature I, vol. 388, p. 860-862. Aug. 1997.*
Li, Jun, et al., "Sol-Gel Transition during Inclusion Complex Formation between α-Cyclodextrin and High Molecular Weight Poly(ethylene glycol)s in Aqueous Solution," *Polymer Journal*, vol. 26, No. 9, pp. 1019-1026 (1994).
Chen, Guohua, and Hoffman, Allan S., "Graft copolymers that exhibit temperature-induced phase transitions over a wide range of pH," *Nature*, vol. 373, pp. 49-52 (Jan. 5, 1995).
Jeoung, Byeongmoon, et al., "Biodegradable block copolymers as injectable drug-delivery systems," *Nature*, vol. 388, 860-862 (Aug. 28, 1997).
Kwon, Ick Chan, et al., "Electrically erodible polymer gel for controlled release of drugs," *Nature*, vol. 354, pp. 291-293 (Nov. 28, 1991).
Leong, K.W., et al., "DNA-polycation nanospheres as non-viral gene delivery vehicles," *Journal of Controlled Release*, vol. 53, pp. 183-193 (1998).
BASF, *Pluronic & Tetronic Surfactants*, BASF Co., Mount Olive, New Jersey, 29 pages (1989).
(Abstract) March, K.L., et al., "Pharmacokinetics of adenoviral vector-mediated gene delivery to vascular smooth-muscle cells—modulation by poloxamer-407 and implications for cardiovascular gene-therapy," *Human Gene Therapy*, vol. 6, No. 1, pp. 41-53 (Jan. 1995).
Loftsson, T., "Increasing the Cyclodextrin Complexation of Drugs and Drug Biovailability through Addition of Water-Soluble Polymers," *Pharmazie*, vol. 53, pp. 733-740 (1998).
Ooya, T. et al., "Synthesis and Characterization of Biodegradable Polyrotaxane as a Novel Supramolecular-structured Drug Carrier," *J. Biomater. Sci. Polymer Edn.*, vol. 8, No. 6, pp. 437-455 (1997).
Ooya, T., et al., "Synthesis of Biodegradable Polymeric Supramolecular Assembly for Drug Delivery," *Macromol. Rapid Commun.*, vol. 16, pp. 259-263 (1995).

(Continued)

*Primary Examiner* — Elli Peselev
(74) *Attorney, Agent, or Firm* — Kilpatrick Townsend & Stockton LLP

(57) ABSTRACT

A cyclodextrin polymer-based injectable composition comprising cyclodextrin, a polymer which is capable of forming a hydrogel with the cyclodextrin, and a pharmacologically effective amount of at least one drug. The polymer is selected from poly(ethylene glycol), derivatives thereon or a copolymer with a poly(ethylene glycol) segment. The copolymer with a poly(ethylene glycol) segment may include a polymer selected from the group consisting of polyesters, polyurethanes, polyamides, polyethers, polysaccharides, poly(amino acid)s, polypeptides, and proteins. The composition may be injected subcutaneously, intramuscularly, intradermally, or intracranially.

39 Claims, 2 Drawing Sheets

OTHER PUBLICATIONS

Jeong, B. et al., "Drug Release from Biodegradable Injectable Thermosensitive Hydrogel of PEG-PLGA-PEG Triblock Copolymers," *Journal of Controlled Release*, vol. 63, pp. 155-163 (2000).

Ooya, T. et al., "Regulation of Intracellular Metabolism by Biodegradable Polyrotaxanes," *J. Biomater. Sci. Polymer Edn.*, vol. 9, No. 4, pp. 313-326 (1998).

Ooya, T. et al., "Synthesis of Theophylline-polyrotaxane Conjugates and Their Drug Release Via Supramolecular Dissociation," *Journal of Controlled Release*, vol. 58, pp. 251-269 (1999).

Ooya, T. et al., "Polyrotaxanes: Synthesis, Structure, and Potential in Drug Delivery," *Critical Reviews in Therapeutic Drug Carrier Systems*, vol. 16, No. 3, pp. 289-330 (1999).

Watanabe, J. et al., "Effect of Acetylation of Biodegradable Polyrotaxanes on its Supramolecular Dissociation Via Terminal Ester Hydrolysis," *J. Biomater. Sci. Polymer Edn.*, vol. 10, No. 12, pp. 1275-1288 (1999).

Yui, N. et al., "Effect of Biodegradable Polyrotaxanes on Platelet Activation," *Bioconjugate Chem.*, vol. 9, No. 1, pp. 118-125 (1998).

Injectable drug-delivery systems based on supramolecular hydrogels formed by poly(ethylene oxide)s and α-cyclodextrin: Jun Li, Xiping Ni, Kam W. Leong: 2003 Wiley Periodicals, Inc. pp. 196-202.

Ceccato, M., et al., "α-CylcoDextrin/Polyethylene Gycol Polyrotaxane: A Study of the Threading Process," *Langmuir*, vol. 13, No. 9, pp. 2436-2439 (1997).

Kamimura, W., et al., "Interaction of Supermolecular Assembly with Hairless Rat Stratum Corneum," *Journal of Controlled Release*, 44, pp. 295-299 (1997).

Ooya, T., et al., "Novel Design of Biodegradable Supramolecular Assembly for Drug Delivery," *Fifth World Biomaterials Congress*, Toronto, Canada, p. 470 (May 29-Jun. 2, 1996).

Watanabe, J., et al., "Preperation and Characterization of Poly(Ethylene Glycol) Hydrogels Cross-Linked by Hydrolyzable Polyrotaxane," *J. Biomater. Sci. Polymer Edn*, vol. 11, No. 12, pp. 1333-1345 (2000).

Yui, N., et al., "Supramolecular-Structured Polymers for Drug Delivery," *Japan Advanced Institute of Science and Technology, School of Materials Science*, pp. 308-309 (1999).

* cited by examiner

INJECTABLE DRUG DELIVERY SYSTEMS WITH CYCLODEXTRIN-POLYMER BASED HYDROGELS

FIELD OF THE INVENTION

The invention is directed to injectable drug delivery systems with cyclodextrin poly(ethylene glycol) polymer based hydrogels.

BACKGROUND OF THE INVENTION

A variety of polymers used for controlled release and deliver of drugs have been developed in the past 20 years. Most of the polymers are formed into implants or injectable microspheres. Such polymers are, and must be, biodegradable and biocompatible.

In order to form suitable forms of polymers, complicated fabrication processes are required which typically involve organic solvents. The use of organic solvents, however, may cause denaturation of some protein drugs and even traces of an organic solvent may be toxic.

Polymer hydrogels have been explored for drug delivery and controlled release. For example, chemically cross-linked polymer hydrogels have been used as implants. Some injectable drug delivery systems form chemically cross-led hydrogels in the body after injection. However, the chemical reactions occurring in The body may cause tissue irritation and damage.

In situ formed hydrogels from thermosensitive block copolymers have also been proposed as sustained release matrix for drugs. They have the advantage that there is no chemical reaction involved in the gel formation. These copolymer hydrogels are usually designed for macromolecular drugs such as protein and hormone drugs. The disadvantage of such temperature sensitive hydrogels is the practicality of using such a gel in injection.

In 1994, June Li and co-workers reported the formation of hydrogels between linear poly(ethylene glycol)s and cyclodextrin. However, since then, there has been few articles on injectable drug delivery systems. In recent years, S. W. Kim et al published a few papers on injectable drug delivery systems using thermosensitive or electrically sensitive hydrogels formed from biodegradable block copolymers.

The article describes poly(ethylene glycol)s (PEG) of high molecular weight which was found to form complexes with alpha-cyclodextrin (alpha-CD) in aqueous solutions to give gels in a wide range of concentration. The time of gelation decreased with increase in alpha-CD and PEG concentration, indicating that the gal formed during complex formation between alpha-CD chains. The time of gelation increases in the molecular weight of PEG, indicating that the PEG chains penetrate alpha CD cavities from the ends of PEG and are included in alpha CDS. X-Ray powder diffraction studies showed that the gel consists of both complexed alpha-CD and uncomplexed alpha CD, indicating partial inclusion of PEG chains by alpha-CD. Further, the gel-melting temperature increased with increases in PEG molecular weight and alpha-CD concentration, and decreased with increase in PEG concentrations, suggesting that gelation results from the formation of longer or shorter domains of alpha-CD-PEG inclusion complexes respectively. (Li J, Harada A Kamachi M., Sol-Gel Transition During Inclusion Complex-Formation between Alpha-Cyclodextrin and High Molecular-Weight Poly(ethylene glycol)s in Aqueous Solution. *Polymer Journal* 26:(9) 1019-1026 1994.

A further article explores polymers as potential drug delivery systems that display a physicochemical response to stimuli. Stimuli studied to date include chemical substances and changes in temperature, pH, and electric field. Homopolymer or copolymers of N-isopropylacrylamide and poly(ethylene oxide)poly(propylene oxide)-poly(ethylene oxide) are typical examples of thermosensitive polymers, but their use in drug delivery is problematic because they are toxic and nonbiodegradable.

Biodegradable polymers used for drug delivery to date have mostly been in the form of injectable microspheres or implant systems, which require complicated fabrication processes using organic solvents. Such systems have the disadvantage that the use of organic solvents can cause denaturation when protein drugs are to be encapsulated. Furthermore, the solid form requires surgical insertion, which often results in tissue irritation and damage, Thermosensitive, biodegradable hydrogels may be synthesized using blocks of poly(ethylene oxide) and poly(L-lactic acid). Aqueous solutions of these copolymers form a sol around 45° C. In this form, the polymer is injectable. On subsequent rapid cooling to body temperature, the loaded copolymer forms a gel that act as a sustained release matrix for drugs. (Jeong B, Bae Y H, Lee D S, Kim S W Biodegradable Block Copolymers as Drug Delivery Systems *Nature* 388:(6645) 860-862 Aug. 28, 1997.)

Another article (Kwon I C, Bac Y H, Kim S W, Electrically Erodible Polymer Gel for Controlled Release of Drugs *Nature* 354:(6351) 291-293 Nov. 28, 1991) is directed to new controlled drug-delivery systems being explored to overcome the disadvantages of conventional dosage forms. For example, stimulated drug delivery has been used to overcome the tolerance problems that occur with a constant delivery rate, to mimic the physiological pattern of hormonal concentration, and to supply drugs on demand. Stimuli sensitive polymers, which are potentially useful for pulsed drug delivery, experience changes in either their structure or their chemical properties in response to change in environmental conditions. Environmental stimuli include temperature, pH, light (ultraviolet or visible), electric field or certain chemicals. Volume changes of stimuli sensitive gel networks are particularly responsive to external stimuli, but swelling is slow to occur. Such systems also provide insight into intermolecular interactions. The polymeric system rapidly changes from a solid state to solution in response to small electric currents, by disintegration of the solid polymer complex into water-soluble polymers. The modulated release of insulin, and by extension other macromolecules, can be achieved with this polymeric system.

It is desired to have an improved hydrogel system for the delivery and controlled release of drugs into the body. It is desired that the process of forming the hydrogel be simple and easy. It is also desired that the properties of the hydrogels be tunable with different copolymers thus allowing delivery and controlled release of a variety of drugs, including protein drugs, and vaccines.

SUMMARY OF THE INVENTION

The invention is directed to a cyclodextrin polymer-based injectable composition comprising cyclodextrin, a polymer which is capable of forming a hydrogel with the cyclodextrin, and a pharmacologically effective amount of at least one drug; wherein the polymer is selected from poly(ethylene glycol), derivatives thereof, or a copolymer with a poly(ethylene glycol) segment The copolymer with a poly(ethylene glycol) segment may include a polymer selected from the group consisting of polyesters, polyurethanes, polyamides, polyethers, polysaccharides, poly(amino acid)s, polypeptides, and proteins. The cyclodextrin may be naturally synthesized by microorganisms or artificially synthesized. The drug is preferably in a pharmaceutically acceptable injectable aqueous fluid.

The invention is further directed to the cyclodextrin polymer-based injectable composition described above and further containing a secondary polymer which complexes with the drug, conjugates the drug, or both. The secondary polymer may be a polymer selected from the group consisting of polyesters, polyurethanes, polyamides, polyethers, polysaccharides, poly(amino acid)s, polypeptides, and proteins. The secondary polymer may be a di- or mono-functional polymer or polyionic polymer with poly(ethylene glycol) segments.

The invention is further directed to a method of treating a condition requiring pharmacological treatment which comprises injecting into the body a cyclodextrin polymer-based injectable composition comprising cyclodextrin a polymer which is capable of forming a hydrogel with the cyclodextrin, and a pharmacologically effective amount of at least one drug; wherein the polymer is selected from poly(ethylene glycol), derivatives thereof, or a copolymer with a poly(ethylene glycol) segment. The injection may be subcutaneous or intramuscular.

DETAILED DESCRIPTION OF THE INVENTION

Figure 1:
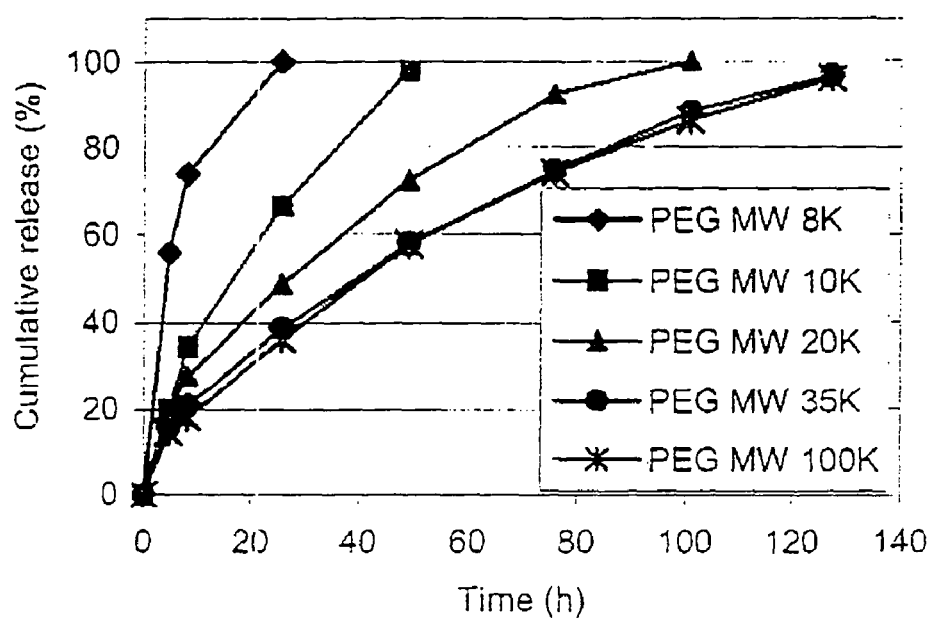
FIG. 1 depicts the release of dextrin-FITC from a hydrogel formed from alphacyclodextrin and linear poly(ethylene glycol) with different molecular weights.

The invention is based on the discovery that gel formation during supramolecular self-assembly between the components forms an injectable hydrogel. Supramolecular self-assembly concerns the spontaneous association of multiple molecular components into a specific phase having well-defined microscopic organization and macroscopic characteristics. It was discovered that drugs can be delivered in a sustained manner from an in vivo matrix or carrier formed from a cyclodextrin polymer-based injectable hydrogel. The injectable composition is a physically cross-linked hydrogel that carries a drug to be released.

The hydrogel is bioabsorbable, thermosensitive, and thixotropic, and and undergoes reversion between gel and sol under certain conditions. Bioabsorbable means the polymer can disappear from its initial application site in the body with or without degradation of the dispersed polymer molecules. The gel-sol transition temperature is generally above room temperature, which depends on the composition of the gel, as well as on the chemical structure and molecular weight of PEG or PEG copolymers.

The formation of the hydrogel is generally very simple and easy. In addition, the properties of the hydrogels are tunable with different copolymers thus allowing delivery of a variety of drugs, including protein drugs, and vaccines, and also allows for the sustained, controlled release of the drugs, genes, vaccines, and the like. For example, the hydrogel gel may be adjusted to be a more flexible hydrogel or a more rigid hydrogen. The hydrogel structure can be tailored to have variable viscosity and drug release rates. Structures with positive charge or with higher hydrophobicity could be used to yield a more sustained release.

The invention is directed to a cyclodextrin polymer-based injectable hydrogel prepared from a cyclodextrin, a polymer capable of forming hydrogel with the cyclodextrin, and at least one drug. The hydrogel provides a sustained, controlled release matrix for the drug.

The drug is in a pharmaceutically acceptable injectable aqueous fluid and may be any drug suitable for injection. Suitable drugs include, but are not limited to, analgesics, anesthetics, antiarthritics, antiasthmas, anticoagulants, anticonvulsants, antidepressants, antidiabetics, antineplastics, antipsychotics, antihypertensives, antibiotics, antihistamines, decongestants, anti-inflammatories, muscle relaxants, peptide drugs, anti-parasitic drugs, antiviral drugs, genes, and vaccines.

The drug is in a macromolecular form or in a low molecular weight form. Low molecular weight drugs may be conjugated to, for example, poly(ethylene glycol) to form a macromolecule. The drug used herein is defined to encompass not only compounds or species which are inherently pharmaceutically or biological active but also material which include one or more of these active compounds or species.

The hydrogel may also carry DNA nanospheres for sustained, controlled release of the DNA nanospheres. DNA nanospheres are nanoparticles synthesized by salt-induced complex coacervation of DNA and polycations such as gelatin and chitosan as gene delivery vehicles (Leong, K W, et al., DNA-polycation nanospheres as non-vial gene delivery vehicles, *Journal of Controlled Release* 53: 183-193, 1998). PEG copolymers with DNA condensing or binding segments may form hydrogels with cyclodextrin, while the polymers condense or bind DNA and form DNA nanospheres in the hydrogels.

The pharmaceutically acceptable injectable aqueous fluid may be, but is not limited to, injectable saline. If desired, the aqueous fluid may also contain buffering agents and/or preservatives. Suitable buffering agents include, but are not limited to, alkali or alkali earth carbonates, phosphates, bicarbonates, citrates, borates, acetates, and succinates. Suitable preservatives include, but are not limited to, sodium bisulfite, sodium thiosulfate, ascorbate, benzalkonium chloride, chlorobutanol, thimersol, phenylmercuric borate, parabens, benzyl alcohol and phenylethanol.

Cyclodextrins are a series of natural cyclic oligosaccharides composed of six, seven, eight, or more D (+) glycopyranose units linked by alpha 1, 4 linkages. Cyclodextrins are biodegradable and biocompatible and may be naturally or artificially synthesized Cyclodextrin may be synthesized naturally by microorganisms, for example. Artificially modified cyclodextrins allow manipulation of its properties to improve their solubility, complex-forming capability, and specificity, and other properties. Cyclodextrin used herein refers to all forms of the natural and artificially modified forms. Suitable cyclodextrins include α-cyclodextrin, β-cyclodextrin, γcyclodextrin and derivatives thereof, including hydrophobic derivatives, hydrophilic derivatives, charged cyclodextrins, and the like.

The polymer is bioabsorbable/biodegradable, biocompatible, and is capable of forming hydrogel with cyclodextrin. Bioabsorbable means the polymer can disappear from its initial application site in the body with or without degradation of the dispersed polymer molecules. Biodegradable means that the polymer can break down or degrade within the body to nontoxic components by hydrolysis or enzymatic degradation. Biocompatible means that all of the components are nontoxic in the body.

The polymer is a poly(ethylene glycol), a derivative thereof, or a copolymer that reacts with the poly(ethylene glycol) segment. The polymer can also be poly(propylene glycol) or other poly(alkylene glycols). Higher molecular weight poly(ethylene glycol) is also called poly(ethylene oxide). Preferably the polymer is poly(ethylene glycol). The copolymer may be any one of a variety of biodegradable and biocompatible copolymers that contain ethylene glycol units which can form hydrogels with cyclodextrins such as polyesters, polyurethanes, polyamides, polyethers, polysaccharides, poly(amino acids), polypeptides, or a proteins.

The poly(ethylene glycol) may have different forms and different end groups. For example, the poly(ethylene glycol) derivatives may have different structures, e.g. star-shaped poly(ethylene glycol), comb-like poly(ethylene glycol), etc. The poly(ethylene glycol) may be modified molecules, e.g. pegylated polysaccharides, pegylated poly(amino acid)s, pegylated proteins, etc. The poly(ethylene glycol) derivatives or copolymers may have poly(ethylene glyol) or polypropylene oxide) segment(s) at the end(s), in which the middle segment carries positive charge. In addition polyamine derivatized poly(ethylene glycol), e.g. pegylated poly(ethylene imine), pegylated polylysine may be used.

Poly(ethylene glycol) block copolymers with poly(propylene oxide), including an pluronic polymers (Poloxamers) may also be used. Different molecular weight of each segments, and weight ratio of the blocks, and different sequences may be used such as PEO-PPO-PEO (Pluronic), PPO-PEO-PPO (Pluronic-R), PEO-PPO, etc.

The molecular weight of the polymer is preferably between 1,000 and 50,000, more preferably between 5,000 and 35,000. Preferably the polymer is in an aqueous solution. For example, typical aqueous solutions contain about 1% to about 80% polymer, preferably about 10% to about 40%. A non-limiting example commercially available is 28% poly(ethylene glycol).

The cyclodextrin and polymer are combined in sufficient amounts and ratios to provide an injectable hydrogel. The hydrogel can be made to pass through needles up to 27 G. Typically, the amount of cyclodextrin to polymer is, but not limited to, 0.275 in weight.

Suitable polymers useful in the invention include PLURONIC (BASF Corp.) surfactant which is a group of poly (ethylene oxide)-polypropylene oxide)poly(ethylene oxide) triblock copolymers also known as poloxamers. The PEG block at both ends is able to complex with α-cyclodextrin, just like the PEG molecules. PLURONIC polymers have unique surfactant abilities and extremely low toxicity and immunogenic responses. These products have low acute oral and dermal toxicity and low potential for causing irritation or sensitization, and the general chronic and subchronic toxicity is low. In fact, PLURONIC polymers are among a small number of surfactants that have been approved by the FDA for direct use in medical applications and as food additives (BASF (1990) Pluronic & Tetronic Surfactants, BASF Co., Mount Olive, N.J.). Recently, several PLURONIC polymers have been found to enhance the therapeutic effect of drugs, and the gene transfer efficiency mediated by adenovirus. (March K L, Madison J E, Trapnell B C. (1995) "Pharmacokinetics of adenoviral vector-mediated gene delivery to vascular smooth muscle cells: modulation by poloxamer 407 and implication for cardiovascular gene therapy." Hum Gene Therapy 6(1): 41-53, 1995).

One skilled in the art recognizes that other related hydrogels can be used. Two functional domains are essential: a poly(ethylene glycol), derivative or copolymer thereof, and a cyclodextrin moiety threaded onto the polymer. A bulky blocking group may be conjugated to the end of polymer chain via a biodegradable linkage, e.g. L-phenylalanine, L-tryptophan, nicotinyl groups, etc. A biodegradable linkage is required for the end group conjugation.

The composition may also contain a secondary polymer which may complex with the drug, conjugate the drug, or both. The secondary polymer may be a polyester, polyurethane, polyamide, polyether, polysaccharide, poly(amino acid), polypeptide, or a protein. Preferably the secondary polymer is a di- or mono-functional polymer or polyionic polymer with polyethylene glycol) segments. In the case where drugs conjugate or complex to the hydrogels, then the hydrogel formulations act not only as a matrix but also a carrier of the drugs. This means that the drug is not only physically entrapped in the hydrogel but also complexed or conjugated to the molecules that form the hydrogel. The secondary polymer may also be used to alter the properties, such as porosity and viscosity, of the matrix hydrogel. The amount of the second polymer should be sufficient to achieve the desired result. e.g. a sufficient amount to complex with and/or conjugate the drug.

The injectable composition may be injected into the body of the patient in any suitable manner. For example, the hydrogen may be administered by subcutaneous, intramuscular, intradermal, and intracranial injection. The hydrogel can be administrated to a confined area or tissue to achieve a higher local concentration of the drug. The particular drug used in the hydrogel is the type which a patient would require for pharmacological treatment of the condition from which the patient is suffering.

The cyclodextrin-polymer based injectable composition may be prepared in any suitable manner. Generally, the drug in aqueous solution is combined with the cyclodextrin. The solution is mixed and then the poly(ethylene glycol) component is added. The mixture is cooled, generally to a temperature of 0° C. to 25° C., preferably to refrigeration temperatures such as 4° C. The resulting pro)duct is a white viscous hydrogel.

The pH of the hydrogel is generally, about 6.5 to about 7.8, which are suitable pH levels for injection into the body. The pH level may be adjusted by any suitable acid or base such as hydrochloric acid or sodium hydroxide.

The following examples are offered by way of illustration and are not intended to limit the invention in any manner.

EXAMPLES

Example 1

Preparation of the injectable hydrogel formulation with linear poly(ethylene glycol) with different molecular weight. In a 0.30 ml of α-cyclodextrin aqueous solution (0.145 g/ml) was dissolved 3.0 mg of fluorescein isothiocyanate labeled dextran (dextran FITC, molecular weight 20,000). The solution was mixed with 0.15 ml of an aqueous solution of PEG (molecular weight from 8,000 to 100,000) with a typical concentration of 0.40 g/ml. The mixture was placed into a 0.6-ml cuvette, and then incubated in a 40° C. water bath for one hour. The cuvette was then kept in a refrigerator at 4° C. overnight, allowing the composition to form a viscous gel.

The resulting gels were injectable hydrogel formulations The gel can pass through needles with different gauges.

Example 2

Release of dextran-FITC from hydrogen forming from alpha cyclodextrin and linear poly(ethylene glycol) with different molecular weights (FIG. 1). For in vitro release studies, the cuvettes with hydrogels prepared in Example 1 were placed upside down in a test tube with 12 ml of water and incubated in a 37° C. water bath. The water was changed in determined intervals of time. The fluorescence intensity was read from 200 microliters samples. Results are plotted in FIG. 1 as cumulative fluorescence released versus time. The values plotted in the figure represent the average of samples from three separate hydrogels. The release rate decreases sharply with an increase in the molecular weight of PEG up to 35,000, presumably because of the chain entanglement effect and different complex stability. The release rate is quite steady with time for gels formed with PEG 35,000 and 100,000.

Example 3

Preparation of the injectable hydrogel formulation with Puronic polymer poly(ethylene glycol)-poly(propylene glycol)-poly(ethylene glycol) with different molecular weights and different ratio between polyethylene glycol) and poly (propylene glycol) segments. In 0.30 ml of α-cyclodextrin aqueous solution (0.145 g/ml) was dissolved 3.0 mg of fluorescein isothiocyanate labeled dextran (dextran-FITC, molecular weight 20,000). The solution was mixed with 0.15 ml of an aqueous solution of Pluronic polymer (molecular weight mom 2,900 to 35,000, PPG/PEG ration between 0 and 3.0) with a typical concentration of 0.40 g/ml. The mixture was placed into a 0.6-ml cuvette, and then incubated in a 40° C. water bath for one hour. The cuvette was then kept in a refrigerator at 4° C. overnight, allowing the mixture to form a viscous gel. The resulting gels were injectable hydrogel formulations. The gel can pass through needles wit different gauges.

Example 4

Figure 2:
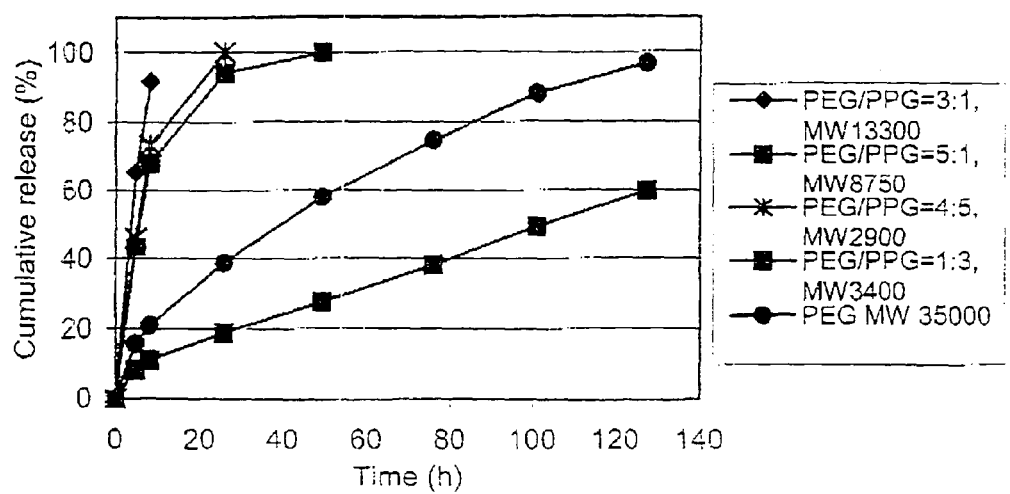
FIG. 2 depicts the release of dextrin-FITC from hydrogels formed from alphacyclodextrin and Pluronic polymer poly(ethylene glycol)-poly(propylene glycol)poly(ethylene glycol) with different molecular weights and different ratios between poly(ethylene glycol) and poly(propylene glycol) segments.

Release of dextran-FITC from hydrogels forming from alpha-cyclodextrin and Pluronic polymer poly(ethylene glycol)poly(propylene glycol)-poly(ethylene glycol) with different molecular weights and different ratios between poly (ethylene glycol) and poly(propylene glycol) segments. (FIG. 2). For in vitro release studies, the cuvettes with hydrogels prepared in Example 3 were placed upside down in a test tube with 12 ml of water and incubated in a 37° C. water bath. The water was changed in determined intervals of time. The fluorescence intensity was read from 200 microliters samples. Results are plotted in FIG. 2 as cumulative fluorescence released versus time. The values plotted in the figure represent the average of samples Tom three separate hydrogels. The result shows that more sustained release kinetics may be obtained with Pluronic polymer PEG-PPG-PEG of lower molecular weight over PEG homopolymer. The higher ratio of PPG segment provides extra intermolecular hydrophobic interaction and reduces the dissolution rate of the gel.

We claim:

1. A cyclodextrin polymer-based injectable composition comprising cyclodextrin, a polymer and a pharmacologically effective amount of at least one drug; wherein the polymer comprises ethylene glycol units and has a molecular weight of 5,000 to 50,000, which forms a hydrogel with the cyclodextrin, wherein the cyclodextrin and the polymer self-assemble to form a hydrogel by spontaneous association and are present in the composition in respective amounts effective to make the hydrogel thixotropic and injectable into the body of a person through a needle, and wherein the hydrogel forms a matrix and entraps the drug such that, when the composition is injected into the body of the person, the drug is released from the hydrogel in a sustained manner.

2. The composition of claim 1, wherein the polymer is selected from the group consisting of star-shaped poly(ethylene glycol) and comb-like poly(ethylene glycol) structures, pegylated polysaccharides, pegylated poly(amino acid)s, pegylated proteins, pegylated poly(ethylene imine), pegylated polylysine, a poly(ethylene glycol) block copolymer with polypropylene oxide), pluronic polymer, poly(ethylene oxide) -poly(propylene oxide)-poly(ethylene oxide), poly (propylene oxide)-poly(ethylene oxide) -poly(propylene oxide) and poly(ethylene oxide)-poly(propylene oxide).

3. The composition of claim 1 wherein the polymer is a copolymer of poly(ethylene glycol) and a polymer selected from the group consisting of polyesters, polyurethanes, polyamides, polyethers, polysaccharides, poly(amino acid)s, polypeptides, and proteins.

4. The composition of claim 1 further comprising a secondary polymer which complexes with the drug, conjugates the drug, or both.

5. The composition of claim 4 wherein the secondary polymer is a di- or mono-functional polymer or polyionic polymer with poly(ethylene glycol) segments.

6. The composition of claim 1 wherein the drug is in a macromolecular form.

7. The composition of claim 1, wherein the drug is selected from the group consisting of analgesics, anesthetics, antiarthritics, antiasthmas, anticoagulants, anticonvulsants, antidepressants, antidiabetics, antineplastics, antipsychotics, antihypertensives, antibiotics, antihistamines, decongestants, anti inflammatories, muscle relaxants, peptides: antiparasitics, antivirals, genes and vaccines.

8. The composition of claim 1, wherein the hydrogel is injectable through a needle of up to 27 gauge.

9. The composition of claim 1, wherein the polymer has a molecular weight of 50,000.

10. The composition of claim 1, wherein the polymer has a molecular weight of between 5,000 and 35,000.

11. The composition of claim 1, wherein the composition comprises an aqueous solution containing the polymer at a level of from about 1% to about 80%.

12. The composition of claim 1, wherein the composition comprises an aqueous solution containing the polymer at a level of from about 10% to 40%.

13. The composition of claim 1, wherein the polymer is selected from the group consisting of pegylated polysaccharides, pegylated poly (amino acids)s, pegylated proteins, pegylated poly(ethylene imine)s and pegylated polylysines.

14. The composition of claim 1, wherein the polymer comprises a poly(ethylene glycol) block or triblock copolymer with poly(propylene oxide).

15. The composition of claim 1, wherein the polymer comprises poly(ethylene oxide).

16. The composition of claim 1, wherein the hydrogel in the composition is thermosensitive and transitions between a gel and a sol at a temperature above room temperature.

17. The composition of claim 1 further comprising DNA nanospheres.

18. The composition as claimed in claim 1, wherein the composition consists essentially of the hydrogel and the drug.

19. A combination comprising:
(a) the composition of claim 1; and
(b) needle means for injecting the composition, with the cyclodextrin and the polymer forming the hydrogel, into the body of a patient.

20. The combination of claim 19, wherein the needle means comprises a needle having a gauge of up to 27 G.

21. A method for administering a drug to a person in need thereof so that it is sustainably released in the body of the person, the method comprising the steps of:
(a) providing the composition of claim 1; and
(b) injecting the composition with the cyclodextrin and the polymer forming the hydrogel through a needle into the body of the person.

22. A method as claimed in claim 21, wherein the method consists essentially of steps (a) and (b).

23. A cyclodextrin polymer-based injectable composition comprising cyclodextrin, a polymer and a pharmacologically effective amount of at least one drug; wherein the polymer is PEG and has a molecular weight of 8,000 to 100,000, which forms a hydrogel with the cyclodextrin, wherein the cyclodextrin and the polymer self-assemble to form a hydrogel by spontaneous association and are present in the composition in respective amounts effective to make the hydrogel thixotropic and injectable into the body of a person through a needle, and wherein the hydrogel forms a matrix and entraps the drug such that, when the composition is injected into the body of the person, the drug is released from the hydrogel in a sustained manner.

24. The composition of claim 23, further comprising a secondary polymer which complexes with the drug, conjugates the drug, or both.

25. The composition of claim 24, wherein the secondary polymer is a di- or mono-functional polymer or polyionic polymer with poly(ethylene glycol) segments.

26. The composition of claim 23, wherein the drug is in a macromolecular form.

27. The composition of claim 23, wherein the drug is selected from the group consisting of analgesics, anesthetics, antiarthritics, antiasthmas, anticoagulants, anticonvulsants, antidepressants, antidiabetics, antineplastics, antipsychotics, antihypertensives, antibiotics, antihistamines, decongestants, anti inflammatories, muscle relaxants, peptides: antiparasitics, antivirals, genes and vaccines.

28. The composition of claim 23, wherein the hydrogel is injectable through a needle of up to 27 gauge.

29. The composition of claim 23, wherein the polymer has a molecular weight is a member selected from the group consisting of 8000, 10,000, 20,000, 35,000, and 100,000.

30. The composition of claim 23, wherein the polymer has a molecular weight of 35,000.

31. The composition of claim 23, wherein the composition comprises an aqueous solution containing the polymer at a level of from about 1% to about 80%.

32. The composition of claim 23, wherein the composition comprises an aqueous solution containing the polymer at a level of from about 10% to 40%.

33. The composition of claim 23, wherein the hydrogel in the composition is thermosensitive and transitions between a gel and a sol at a temperature above room temperature.

34. The composition of claim 23, further comprising DNA nanospheres.

35. The composition as claimed in claim 23, wherein the composition consists essentially of the hydrogel and the drug.

36. A combination comprising:
(a) the composition of claim 23; and
(b) needle means for injecting the composition, with the cyclodextrin and the polymer forming the hydrogel, into the body of a patient.

37. The combination of claim 36, wherein the needle means comprises a needle having a gauge of up to 27 G.

38. A method for administering a drug to a person in need thereof so that it is sustainably released in the body of the person, the method comprising the steps of:
(a) providing the composition of claim 23; and
(b) injecting the composition with the cyclodextrin and the polymer forming the hydrogel through a needle into the body of the person.

39. The method of claim 38, wherein the method consists essentially of steps (a) and (b).

* * * * *